United States Patent [19]

Schindler et al.

[11] 4,206,027

[45] Jun. 3, 1980

[54] MULTI-PROBE MEASURING UNITS AND ISOLATION MEMBERS THEREFOR

[75] Inventors: Johannes G. Schindler, Marburg an der Lahn; Wilfried Schäl, Bad Homburg; Heinz E. Braun, Hachborn, all of Fed. Rep. of Germany

[73] Assignee: Dr. E. Fresenius Chemisch pharmazeutische Industrie KG, Apparatebau KG, Bad Homburg, Fed. Rep. of Germany

[21] Appl. No.: 915,222

[22] Filed: Jun. 13, 1978
(Under 37 CFR 1.47)

[30] Foreign Application Priority Data

Jun. 14, 1977 [DE] Fed. Rep. of Germany ....... 2726772

[51] Int. Cl.² .............................................. G01N 27/46
[52] U.S. Cl. ............................. 204/195 R; 204/195 P; 204/195 M
[58] Field of Search ........... 204/195 R, 195 F, 195 G, 204/195 M

[56] References Cited

U.S. PATENT DOCUMENTS

| 2,886,771 | 5/1959 | Vincent | 204/195 R |
| 3,151,052 | 9/1964 | Arthur et al. | 204/195 F |
| 3,290,584 | 12/1966 | Harms et al. | 204/195 R |
| 3,498,289 | 3/1970 | Watanabe et al. | 204/195 F |
| 3,556,950 | 1/1971 | Dahms | 204/195 R |
| 3,997,420 | 12/1976 | Buzza | 204/195 G |

Primary Examiner—T. Tung
Attorney, Agent, or Firm—Omri M. Behr

[57] ABSTRACT

A multiple measurement system for the electrochemical analysis of fluids and gases includes a housing adapted to receive a plurality of isolating members which are firmly held in position in the housing. The housing and isolating members are adapted to receive measurement-probes, each of which extends into the isolating member and is in intimate contact with a measurement chamber provided therein. Inflow and outflow openings or channels communicating with the measurement chamber are provided in the insulating members. The end surfaces of each insulating member and the contact surface of a pair of end members are frusto-conically shaped to provide intimate contact between touching surfaces of the isolating and end members. The inflow and outflow channels or openings provided in the isolating members and end members are in alignment and provide a continuous fluid flow path from input to output.

15 Claims, 3 Drawing Figures

MULTI-PROBE MEASURING UNITS AND ISOLATION MEMBERS THEREFOR

BACKGROUND OF THE INVENTION

Many multiple measurement systems for electrochemical analysis of fluids and gases are known in the prior art. Typical of these devices is German Published patent application No. (OLS) P2,652,370.6 and J. G. Schindler, Biomed. Techn. 22, 235, (1977) which are incorporated herein in their entirety.

The major problems inherent with the prior art devices are their relatively large size and their inability to maintain a proper leak-proof surface interface between the adjoining insulating members.

The preferred embodiment of the present invention overcomes these shortcomings by providing a relatively small multiple measurement system with virtually leak-proof surfaces between the adjoining isolating members.

SUMMARY OF THE INVENTION

A multiple measurement system for the electrochemical analysis of fluids and gases, according to the principles of the present invention, comprises, in combination: a hollow elongated housing, the housing having a longitudinal axis, an inflow opening at one end, an outflow opening at the other end thereof and a plurality of openings adapted to receive measurement probes therein disposed along the longitudinal axis and transverse thereto; a plurality of isolating members adapted to be received by the hollow housing. Each of the isolating members are provided with the following: frusto-conical end surfaces positioned transverse to the longitudinal axis, an inflow and outflow through opening, a measurement chamber communicating with the inflow and outflow through opening, and a transverse opening communicating with the measurement chamber positioned for alignment with one of the housing probe openings and adapted to receive a measurement probe therein. Also included is a pair of end members, each having a through opening, one of the pair of end members is disposed proximate the inflow opening of the housing and the other end member is disposed proximate the outflow opening of the housing with a plurality of isolating members being disposed therebetween. Furthermore, retaining means are included for retaining the pair of end members and the plurality of isolating members in intimate contact therebetween with all the inflow and outflow openings in alignment and forming a continuous flow path.

BRIEF DESCRIPTION OF THE DRAWINGS

In order that the invention may be more fully understood, it will now be described, by way of example, with reference to the accompanying drawing in which.

DESCRIPTION OF THE PREFERRED EMBODIMENT

Figure 1:
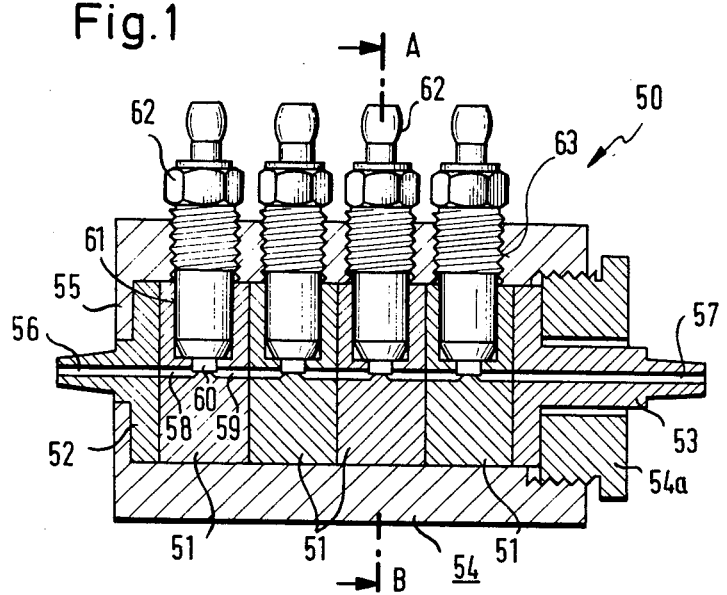
FIG. 1 is a cross-section in elevation of the multiple measurement system, according to the principles of the present invention.

Referring now to the figures and, in particular, to FIG. 1 in which a multiple measurement system 50 is shown in cross-section. The multiple measurement system 50 includes a plurality of isolating members 51 held in intimate contact by a pair of end members 52 and 53 within a hollow elongated housing 54. The housing 54 is provided with an opening 80 at one end and a retaining portion 55 which includes an aperture 88 at the other end thereof. An elongated generally conically-shaped portion 82 of end member 52 extends through aperture 88 of the housing 54 and is adapted to be inserted into hollow tubing, not shown. A through opening, aperture or channel 56 is provided in the end member 52, the purpose thereof will be explained hereinafter.

An externally threaded nut member 54a is adapted to cooperate with internal threads 84 provided in opening 80 of the housing 54. Nut member 54a is also provided with a centrally disposed aperture 86 through which an elongated portion 90 of end member 53 extends. End member 53 is adpated to be inserted into hollow tubing, not shown, and is also provided with an opening, aperture or channel which is preferably centrally disposed along the longitudinal axis X—X of the multiple measurement system 50.

Figure 2:
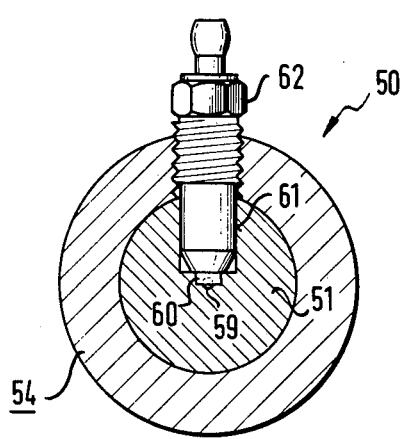
FIG. 2 is a section in elevation taken along the line A—A of FIG. 1.
Figure 3:
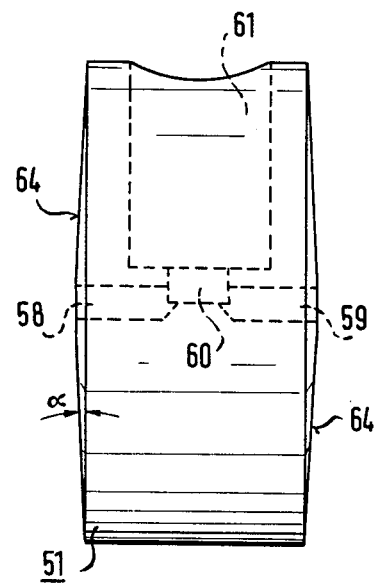
FIG. 3 is an enlarged front view in elevation of one isolating member incorporating the features of the present invention.

The isolating member 51 is shown more clearly in FIG. 3 and includes inflow and outflow channels, apertures or openings 58 and 59, respectively. Centrally disposed in each isolated member is the measurement chamber 60 which is provided with openings 78 and 79 in the ends thereof, permitting communication with the apertures 58 and 59. The apertures 58 and 59 are centrally disposed and preferably will coincide with the longitudinal axis X—X when installed in the housing 54. In addition, a bore, opening or aperture 61 positioned transverse to the longitudinal axis X—X is provided in the isolating member. The lower portion 92 of opening 61 is adapted to form an intimate sealing contact with the bottom surface 91 (FIG. 2) of the measurement probe 62 inserted therein.

The probe 62 is preferably provided with a threaded portion 94 which is adapted to cooperate with the threaded apertures or openings 63 provided in the housing 54. Apertures 63 are transverse to the longitudinal axis X—X spaced therealong.

In addition, the isolating member 51 is provided with frusto-conical end surfaces 64 which form an angle $\phi$ with its base 65 shown in FIG. 3. The angle $\phi$ should be less than 5 degrees with respect to its base and preferably should range from 0.5 to 1.0 degrees.

FIG. 2 clearly discloses the probe 62 threaded into the opening 63 of the housing 64 and cooperating with the opening 61 provided in the isolating member 51.

The multiple measurement system may readily be assembled in the following manner. End member 52 is inserted in the hollow or open portion of housing 54 with its elongated portion 82 extending through aperture 88. A plurality of isolating members are inserted in the hollow opening of housing 54 such that the opening 61 is made to align with the opening 63 of the housing 64. The other end member 53 is inserted within the hollow opening of the housing 54 with the elongated portion 90 extending out of opening 80, thereby sandwiching the isolating members therebetween.

Preferably, a nut member 54a, externally threaded is then inserted over the elongated portion 90 of end member 53 and caused to threadedly engage the internal threads 84 provided in the housing 54. The rotation of nut member 54a in the proper direction will cause end member 53 to exert pressure, via its contact surface 70, on the end surface 64 of isolating member 51. This causes all the isolating members in turn to exert pressure on the adjoining isolating member until the pressure is transferred to end member 52, which is retained in position by retaining portion 55 of the housing 54. A slight compressing of the conical surface 64 occurs at this pressure is exerted. It is to be noted that the contact surfaces 70 and 71 of end members 52 and 53, respectively, may also be provided with a similarly frusto-conically shaped surface as that disclosed for the isolating members. Preferably, the openings 56, 57, 58 and 59 lie on the longitudinal axis X—X of the measurement system 50, thereby providing a continuous flow path which includes the measurement chamber 60 provided in each of the isolating members 51.

A measurement probe 62 is inserted into each of the openings 63 provided in the housing 54 and is readily engaged therein. Rotation of probe 62 in the proper direction causes it to advance into opening 63 until its bottom surface 91 comes into contact with and surrounds the surface 92, closing off and sealing the measurement chamber. Thus, the continuous flow path from inflow 56 to outflow 57 is not interrupted.

The present invention is not limited to the particular type of probe as shown, and of course the internal structure of the probe may be varied in order to accomplish a particular measurement. The only probe requirement is that the bottom surface 92 thereof be such that it will seal the measurement chamber when inserted therein.

It is also to be noted that a probe having a similar outer configuration as disclosed but having a through aperture may be utilized to provide an auxiliary flow path of the gas or fluid flowing from opening 56 to 57. This provides an auxiliary path for additional measurements, which can take on any number of configurations. For example, if one multiple measurement system is connected to another via a hollow tube, not shown, a configuration resembling the letter "V" may be formed or an "H" may be obtained with a pair of parallel flow paths with a hollow tube connected therebetween.

In the preferred embodiment of the present invention the housing 54, the nut member 54a and probes 62 are fabricated from metal. The isolating members 51 and end members 52 and 53 are preferably fabricated from polyacrylic glass.

Hereinbefore has been disclosed a multiple measurement system which overcomes the shortcomings of the prior art and provides a continuous, leakage-free flow path. Provision has also been made for replacing the isolating members, since it is obvious that they may be readily removed from the housing 54 and replaced if they should become worn or contaminated.

It will be understood that various changes in the details, materials, arrangement of parts and operating conditions which have been herein described and illustrated in order to explain the nature of the invention may be made by those skilled in the art within the principles and scope of the present invention.

Having thus set forth the nature of the invention, what is claimed is:

1. A multiple measurement system for the electrochemical analysis of fluids and gases comprising, in combination:

(a) a hollow elongated housing, said housing having a longitudinal axis, an inflow opening at one end, an outflow opening at the other end thereof, and a plurality of openings adapted to receive measurement probes therein disposed along said longitudinal axis and transverse thereto;

(b) a plurality of isolating members adapted to be received by said hollow housing, each said isolating member being provided with;
  (i) frusto-conical end surfaces positioned transverse to said longitudinal axis,
  (ii) an inflow and outflow through opening,
  (iii) a measurement chamber communicating with said inflow and outflow through opening, and
  (iiii) a transverse opening communicating with said measurement chamber positioned for alignment with one of said housing probe openings and adapted to receive a measurement probe therein, (c) a pair of end members each having a through opening, one of said pair of end members being disposed proximate said inflow opening of said housing and the other end member being disposed proximate said outflow opening of said housing with a plurality of isolating members being disposed therebetween, and (d) means for retaining said pair of end members and said plurality of isolating members in intimate contact therebetween with all said inflow and outflow openings in alignment forming a continuous flow path.

2. In a multiple measurement system for the electrochemical analysis of fluids and gases having a longitudinal axis and including a housing and isolating members adapted to receive measurement probes therein, said isolating members being adapted for insertion into said housing, each said isolating member comprising:

(a) frusto-conical end surfaces adapted to be positioned transverse to said longitudinal axis,
(b) an inflow and outflow through opening,
(c) a measurement chamber communicating with said inflow and outflow through opening, and
(d) a transverse opening communicating with said measurement chamber and adapted to receive said measurement probe.

3. An isolating member according to claim 2 wherein each said frusto-conical end surface forms an angle of less than 5 degrees with respect to its base.

4. A multiple measurement system for the electrochemical analysis of fluids and gases comprising, in combination:

(a) a hollow elongated housing, said housing having a longitudinal axis, an opening at one end, an aperture at the other end thereof, and a plurality of threaded apertures disposed along said longitudinal axis and transverse thereto;

(b) a plurality of isolating members adapted to be received by said hollow housing, each said isolating member being provided with;
  (i) frusto-conical end surfaces positioned transverse to said longitudinal axis,
  (ii) a through aperture,
  (iii) a measurement chamber communicating with said through aperture; and
  (iiii) a transverse aperture communicating with said measurement chamber positioned for alignment with one of said transverse housing apertures, (c) a measurement probe, said probe having a threaded portion adapted to cooperate with said housing threaded aperture, extending into said isolating member transverse aperture and in intimate contact with said measurement chamber, (d) a pair of end members each having a through aperture, one of said pair of end members being disposed proximate said housing other end, the other end member disposed proximate said housing one end with said plurality of isolating members positioned therebetween, and (e) means for retaining said pair of end members and said plurality of isolating members in intimate contact therebetween with all said through apertures in longitudinal alignment within said housing.

5. A measurement system according to claim 4 wherein said housing is tubular-shaped and said housing transverse threaded apertures extend through the wall of said tubular-shaped housing.

6. A measurement system according to claim 4 wherein said isolating members are circularly-shaped having a diameter approximately equal to the inner diameter of said housing.

7. A measurement system according to claim 4 wherein said through apertures are aligned parallel to said longitudinal axis.

8. A measurement system according to claim 7 wherein said through apertures are centrally disposed and concentric with said longitudinal axis.

9. A measurement system according to claim 4 wherein said measurement probe seals said measurement chamber at their mutual point of contact.

10. A measurement system according to claim 4 wherein said housing is provided with a threaded portion at said open one end and said retaining means includes an externally threaded nut adapted to cooperate with said threaded housing end for exerting longitudinal compressive forces on said end members and said isolating members.

11. A measurement system according to claim 10 wherein said end members extend through said housing other end and the opening in said nut.

12. A measurement system according to claim 4 wherein said housing, said nut and said probe are fabricated of metal and said isolating members are fabricated of polyacrylic glass.

13. A measurement system according to claim 4 further including a take-off probe externally dimensioned identical to a measurement probe and having a through aperture communicating with said measurement chamber and the external environment.

14. A measurement system according to claim 4 wherein each said frusto-conical end surface forms an angle of less than 5 degrees with respect to its base.

15. A measurement system according to claim 4 wherein each said frusto-conical end surface forms an angle of from 0.5 to 1.0 degree with respect to its base.

* * * * *